United States Patent [19]

Schlör et al.

[11] Patent Number: 5,531,802

[45] Date of Patent: Jul. 2, 1996

[54] SUCTION DEVICE WITH A FILTER INSERT IN THE SUCTION LINE

[75] Inventors: Georg Schlör, Lübeck; Hans-Karsten Reimers, Hamberge; Dietrich Vosberg, Lübeck; Holmer Röhling, Reinfeld, all of Germany

[73] Assignee: Drägerwerk Aktiengesellschaft, Lübeck, Germany

[21] Appl. No.: 236,455

[22] Filed: May 2, 1994

[30] Foreign Application Priority Data

May 29, 1993 [DE] Germany .................. 43 18 021.3

[51] Int. Cl.⁶ .................................................. B01D 46/24
[52] U.S. Cl. .................. 55/274; 55/356; 55/467; 55/498; 55/521; 55/DIG. 3
[58] Field of Search ............ 55/498, 497, 492, 55/357, 356, DIG. 3, 482, 521, 274, 467

[56] References Cited

U.S. PATENT DOCUMENTS

| | | | |
|---|---|---|---|
| 3,169,843 | 2/1965 | Campbell | 55/498 |
| 4,172,709 | 10/1979 | Kippel. | |
| 4,314,832 | 2/1982 | Fox | 55/482 |
| 4,701,193 | 10/1987 | Robertson. | |
| 4,986,839 | 1/1991 | Wertz et al. | 55/274 |
| 5,112,372 | 5/1992 | Boeckermann et al. | 55/276 |
| 5,125,940 | 6/1992 | Stanhope et al. | 55/385.3 |

FOREIGN PATENT DOCUMENTS

| | | |
|---|---|---|
| 1695409 | 3/1955 | Germany. |
| 1762340 | 2/1958 | Germany. |
| 8327743.9 | 11/1983 | Germany. |
| 4121069A1 | 2/1992 | Germany. |
| 795226 | 5/1958 | United Kingdom. |
| 1201156 | 8/1970 | United Kingdom. |
| 21A1967 | 5/1987 | United Kingdom. |

Primary Examiner— Romulo H. Delmendo
Attorney, Agent, or Firm—McGlew & Tuttle

[57] ABSTRACT

A device with an extraction fan for use for drawing off ambient air loaded with harmful substances during, e.g., laser surgery or HF surgery, is passed through a filter device. For routine use, easy replacement of the filter should be possible, its loading time is prolonged, and the arrangement of the filter does not compromise the easy handling of the suction line. To achieve this, a transparent sleeve 6, into which a cylindrical folded filter 10 is pulled via a perforation support tube 26, is installed in the suction line, or the filter has a hole 29 provided with a support lining, so that the filter can be directly attached to the suction-side connecting branch 5. The filter 10 is flown through radially, and thus it offers a large filter surface at minimum extension.

19 Claims, 3 Drawing Sheets

SUCTION DEVICE WITH A FILTER INSERT IN THE SUCTION LINE

FIELD OF THE INVENTION

The present invention pertains to a device with an extraction fan, which guides ambient air loaded with harmful substances via a suction line into a filter device for separating the pollutants.

BACKGROUND OF THE INVENTION

Such devices are used especially in the area of laser and high-frequency surgery, which are intended to effectively remove fumes and viruses or bacteria generated during surgery in the area of operation. To achieve this, a suction snorkel, which is attached to a suction line, is held in the immediate vicinity of the laser scalpel, so that the harmful substances generated are immediately removed and retained in a filter device. To do so, a preliminary filter for retaining suspended matter or aerosol particles, which is followed by a larger bacteria and odor filter on the inlet side to the extraction fan, is usually inserted in the suction line.

Such a device has become known from German Offenlegungsschrift No. DE-OS 41 21 069. The filter inserts located in the suction line are arranged either at the end of the suction line, if necessary, downstream of a preceding liquid trap, in which case a rather long section of the suction line is exposed to unfiltered, contaminated intake air, or the filter is arranged, to the extent possible, at the front of the suction opening. In the latter case its ease of handling is, however, compromised, so that it must have a large volume, as a result of which its separation capacity is low.

SUMMARY AND OBJECTS OF THE INVENTION

The basic object of the present invention is to improve a device of the above-mentioned type such that easy replacement of a filter is possible, while its loading time is prolonged, and the arrangement of the filter does not compromise the ease of handling of the suction line.

The object is attained, on the one hand, by arranging an essentially cylindrical sleeve, which can be inspected and is supported in a suction-tight manner at its front-side openings via two connecting pieces, in the suction line, and by connecting the suction-side connecting piece to a rod-shaped, perforated support tube, to which an essentially cylindrical folded filter can be attached, and the front surfaces of the folded filter are otherwise impermeable in the direction of flow, so that the ambient air is drawn into the support tube radially from the outside through the filter.

This object is also attained by the fact that the suction line contains an essentially cylindrical, inspectable sleeve, which is supported at its front-side openings in a suction-tight manner via two connecting pieces, and which accommodates an essentially cylindrical filter, which has a central, axially extending hole, which passes through one of the two, otherwise impermeable front walls in the form of a connecting branch, via which the filter can be attached to the suction-side connecting piece in a suction-tight manner, so that the ambient air is drawn into the hole through the filter radially from the outside.

The advantage of the present invention is essentially the fact that it is always possible during the handling of the suction line to observe whether the filter has been loaded or whether it still has sufficient capacity. If the filter must be replaced, the handpiece can be taken apart and the filter can be replaced in a simple manner. A large filter surface at the smallest possible volume can be obtained due to the cylindrical shape of the folded filter and to the fact that it is flown through radially from the outside to the inside. The suction capacities of extraction fans have been known to be designed such that a large-surface filter would lose its stability, were it not reinforced by a central support tube. However, if the filter is stabilized in its suction-side, central hole itself by suitable means, e.g., the shape of the folds or supporting insert rings, a separate support tube can be omitted, and the filter can be directly provided with a connecting branch, via which it can be attached to the suction-side connecting piece. When the filter is replaced, the filter does not first have to be pulled off from the support tube, but it can be removed directly from the handpiece.

The filter is preferably provided with a support lining in its cylindrical hole, so that a separate support tube at the connecting piece can be omitted.

The sleeve is advantageously designed as a handpiece, which is directly connected to the connecting piece provided with a suction snorkel. It is achieved as a result that the handling of the suction line and the guiding of the suction snorkel are simplified, and that the space provided for the handpiece is filled by arranging an additional filter. A cylindrical handpiece fits the hand better and is easier to guide, and it also fails to hinder the suction flow as strongly as would a filter of a prior-art shape, e.g., an angular or disk-shaped filter.

To simplify disassembly and replacement of the filter, the connecting pieces are designed as attachable connecting pieces. Suitable sealing elements, e.g., O-ring seals, are provided for the suction-tight connection.

One of the front surfaces, namely, that facing away from the suction side and consequently facing the suction snorkel, is designed at the filter such that it is used as an impact surface for the harmful substances drawn off, because the harmful substances drawn off may have different size distributions, and they may also be, among other things, solid aerosol particles, which will adhere to the impact surface, rather than blocking the filter surface. In the simplest case, the impact surface is a flat front surface, but it may also be concave in its center, or it may also have a capture edge on its circumference to ensure that the particles captured will adhere to the impact surface for a rather long time. A filter change should usually be performed after a use time of 20 to 30 minutes.

Since the suction snorkel is usually a narrow-lumen tube, it is favorable for the connecting piece for the suction snorkel to open conically toward the interior of the sleeve to achieve a favorable flow distribution around the circumference of the filter and to utilize the front-side impact surface of the filter as uniformly as possible.

If it is advantageous to accommodate the filter in the sleeve designed as a handpiece, the advantage of the present invention can also be utilized, on the other hand, even when the sleeve with the cylindrical folded filter and with the other features of the present invention is arranged elsewhere in the suction line.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DETAILED DESCRIPTION OF THE PREFERRED EMBODIMENTS

Figure 1:
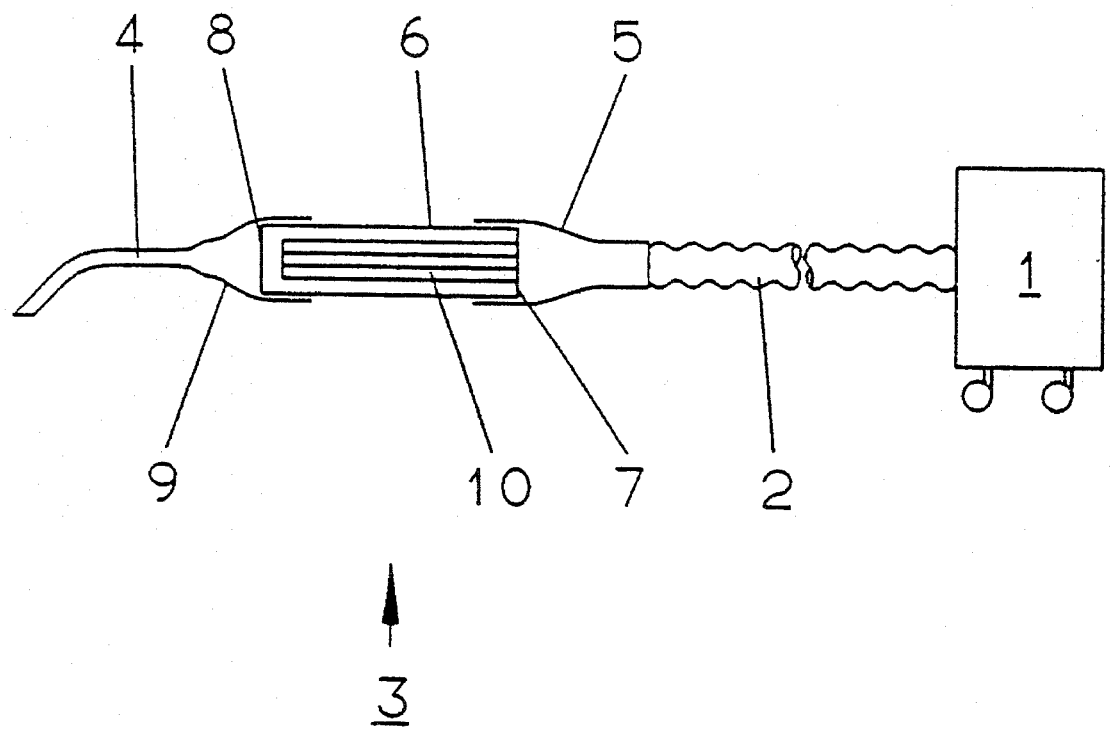
FIG. 1 is an overall representation of a suction device.

The portable suction device is represented in FIG. 1. The functional components are a portable extraction fan 1, and filter means, connected to a suction line 2, whose end is connected to a handpiece 3, which is joined by a suction snorkel 4. The suction line 2 is connected via a downstream connecting piece 5 to a cylindrical and transparent sleeve 6, whose front-side opening 7 is inserted into the connecting piece 5. On the other side, the sleeve 6 is attached with its front-side opening 8 to another or upstream connecting piece 9, which in turn carries the suction snorkel 4. The interior of the sleeve 6 accommodates a filter 10, which is designed as an axial folded filter, whose structure is explained in greater detail in FIGS. 2 and 3.

Figure 2:
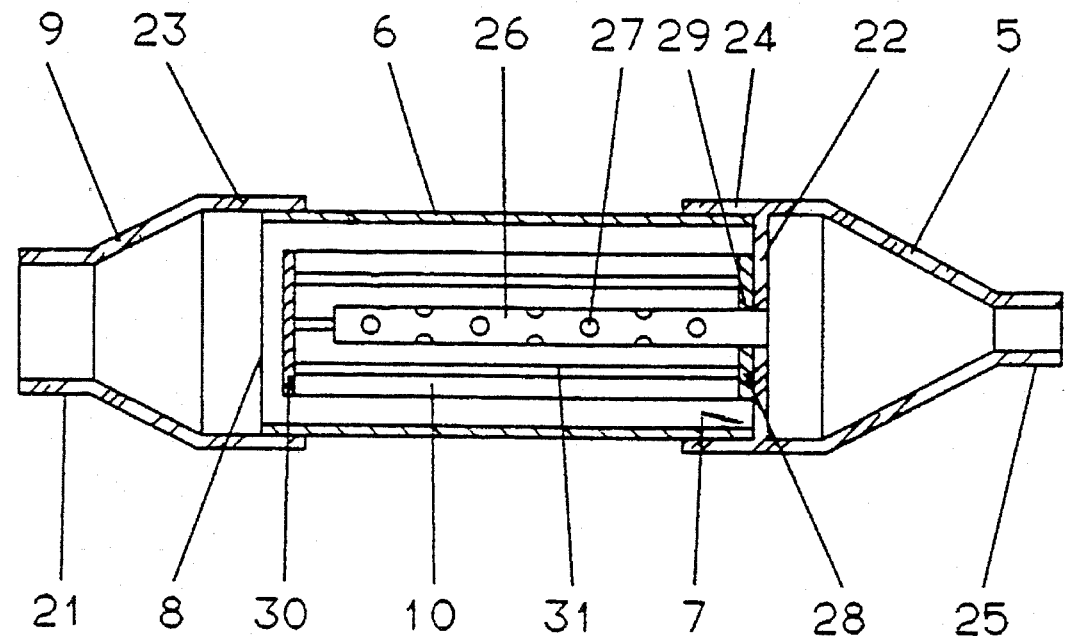
FIG. 2 is a sectional view through a handpiece with inserted filter.

FIG. 2 shows the detail of the handpiece 3, whose transparent sleeve 6 can be grasped by the hand of the user of the device. The sleeve 6 is inserted, with one of its the front-side openings 8, into a collar 23 of the connecting piece 9, whose muff 21 is to be connected to the suction snorkel 4, not shown. The opposite front-side opening 7 of the sleeve 6 abuts a connection wall 22 of the connecting piece 5, and is accommodated in its attached collar 24. The connection socket 25 of the connecting piece 5 is connected to the suction line 2, not shown. A support tube 26, extends axially to the sleeve 6 and is provided with perforations 27. The support tube 26 has a connection branch portion accommodated in the connection wall 22. The folded filter 10 is attached to the perforated support tube 26, which extends over nearly the entire length of the filter, via a filter hole 29 provided in a front surface or downstream end wall 28 of the folded filter 10. The front surface 28 provided with the hole 29 sits closely to the connection wall 22. Another front surface or an upstream end wall 30 of the filter 10 is designed as an impact surface means and is, like the front surface 28, impermeable around the hole 29. The folds 31 of the filter 10 extend axially in parallel to both the sleeve 6 and the support tube 26.

Figure 3:
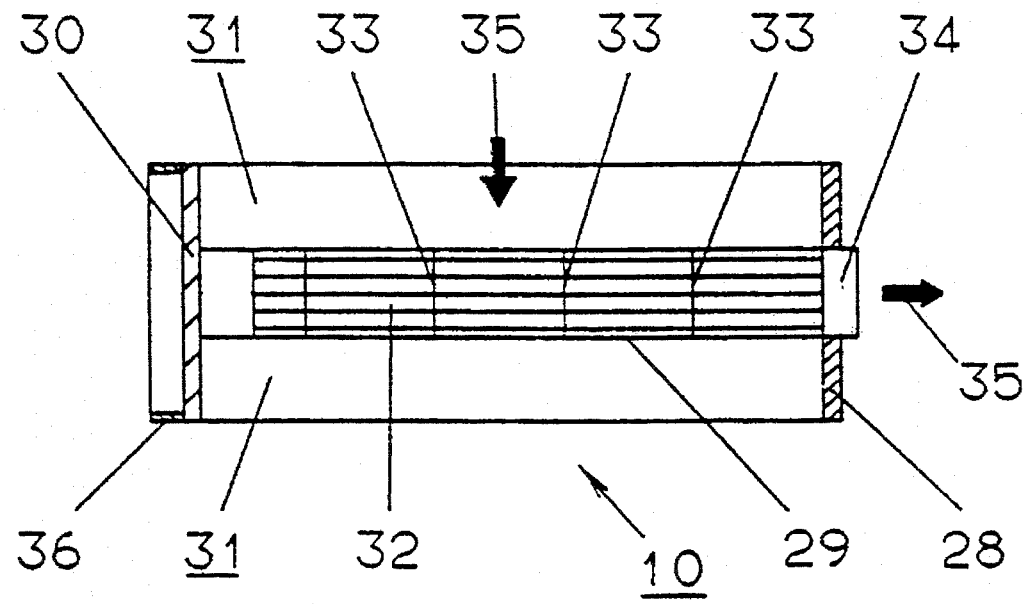
FIG. 3 is a sectional view of another embodiment of a filter.

FIG. 3 shows another embodiment of the folded filter 10. The folds 31 are edged between the impermeable front surfaces 28, 30 and exit along the hole 29. This is indicated by the fold line 32. The hole 29 carries a support lining in the form of webs 33, which hold the folds 31 along their fold lines 32 at a predetermined distance and maintain a stable diameter of the hole 29 even under the suction effect of the suction device 1. However, other support elements, e.g., support cages introduced separately for the dimensional stabilization of the filter element, are also imaginable. The hole 29 terminates at the front surface 28 with a connecting branch 34, which penetrates into a corresponding perforation in the connection wall 22 according to FIG. 2 in the installed state of the filter 10. It is now possible to omit the support tube 26, which was still necessary in the embodiment according to FIG. 2. In the installed state, the ambient air flows through the filter according to FIG. 3 in the same manner as in the filter according to FIG. 2, i.e., along the flow arrows 35. The ambient air is drawn in by the fan radially into the filter 10, and it leaves at the hole 29. The ambient air thus filtered leaves axially at the connecting branch 34 and is drawn off. Coarser particles and aerosol particles are captured on the upstream impact surface means 30 of the filter 10. The impact surface 30 is surrounded by an edge 36 to prevent particles located on the impact surface 30 from being carried away by the flow and from being deposited in the folds 31 of the filter 10.

While specific embodiments of the invention have been shown and described in detail to illustrate the application of the principles of the invention, it will be understood that the invention may be embodied otherwise without departing from such principles.

What is claimed is:

1. A suction device comprising:

a suction line;

a substantially cylindrical sleeve with end openings;

an upstream side connecting piece and a downstream side connecting piece supporting said cylindrical sleeve in a suction-tight manner adjacent said end openings, said cylindrical sleeve being provided in said suction line;

a rod-shaped perforated support tube connected to said downstream connecting piece; and a substantially cylindrical folded filter having a nonpermeable front surface aligned in a direction of flow, said cylindrical folded filter being attached to said perforated support tube whereby ambient air is drawn into said support tube radially from outside, through said filter whereby said filter separates harmful substances from ambient air;

a suction snorkel positioned on said upstream connecting piece.

2. A suction device comprising:

a suction line with a substantially cylindrical sleeve formed of a material for observing through said sleeve;

an upstream side connecting piece and a downstream side connecting piece holding said cylindrical sleeve in a suction-tight manner;

a substantially cylindrical filter with a central axially extending hole, said cylindrical filter having two non-permeable end walls wherein said central axially extending hole exits through one of said end walls, said nonpermeable end walls are aligned in a direction of flow, said end wall with said axially extending hole includes a connection branch via which said filter can be attached to said downstream side connecting piece in a suction-tight manner, whereby ambient air is drawn into said hole through said filter radially from an outside of said filter: a suction snorkel positioned on said upstream side connecting piece.

3. A device according to claim 2, wherein:

said hole has a support lining.

4. A device according to claim 1, wherein:

said sleeve is designed as a handpiece and directly connected to said upstream side connecting piece.

5. A device according to claim 2, wherein:

a said sleeve is designed as a handpiece and directly connected to said upstream side connecting piece.

6. A device according to claim 1, wherein:

said upstream side connecting piece and said downstream side connecting piece are designed as detachable connecting pieces.

7. A device according to claim 2, wherein:

said upstream side connecting piece and said downstream side connecting piece are designed as detachable connecting pieces.

8. A device according to claim 1, wherein:

said filter has an upstream end surface formed as an impact surface for drawing off harmful substances.

9. A device according to claim 2, wherein:

said filter has an upstream end surface formed as an impact surface for drawing off harmful substances.

10. A device according to claim 4, wherein:

said upstream connecting piece for said suction snorkel conically opens toward an interior of said sleeve.

11. A device according to claim 5, wherein:

said upstream connecting piece for said suction snorkel conically opens toward an interior of said sleeve.

12. A suction device comprising:

a suction passage including a suction line;

a downstream connecting piece positioned in said suction passage said downstream connecting piece including a support wall defining an opening;

a sleeve connected to an upstream end of said downstream connecting piece;

an upstream connecting piece connected to an upstream end of said sleeve;

a substantially cylindrical filter having a downstream end wall with a contact branch connected to said downstream connecting piece, said filter defining a central axially extending filter hole in communication with a cavity defined by said downstream connecting piece, an area radially outside of said filter being in communication with a cavity defined by said upstream connecting piece, said contact branch being fitted into said opening of said support wall.

13. A device in accordance with claim 12, wherein:

said sleeve is formed as said handpiece;

said downstream connecting piece is connected to an upstream end of said suction line;

said upstream connecting piece is provided with a suction snorkel.

14. A device in accordance with claim 12, wherein:

said filter includes an upstream end wall formed of impermeable material and including impact surface means for capturing particles.

15. A device in accordance with claim 12, wherein:

said upstream connecting piece, said sleeve and said downstream connecting piece are aligned with an axis of said substantially cylindrical filter.

16. A device in accordance with claim 12, wherein:

said handpiece is movable in a vicinity of a laser scalpel.

17. A device in accordance with claim 12, further comprising:

a support lining in said filter hole.

18. A device in accordance with claim 12, wherein:

said contact branch is part of a perforated support tube extending into said filter hole, said support tube being attached to said filter.

19. A device in accordance with claim 12, wherein:

said sleeve is transparent and formed as said handpiece;

said downstream connecting piece is connected to an upstream end of said suction line;

said upstream connecting piece is provided with a suction snorkel;

said filter includes an upstream end wall formed of impermeable material and including impact surface means for capturing particles;

said upstream connecting piece, said sleeve and said downstream connecting piece are aligned with an axis of said substantially cylindrical filter;

said handpiece is movable in a vicinity of a laser scalpel;

said downstream connecting piece includes a support wall defining an opening, and said contact branch is fitted into said opening;

said filter is a folded filter;

an extraction fan is connected to a downstream end of said suction line.

* * * * *